United States Patent [19]

Ishii

[11] Patent Number: 4,576,144
[45] Date of Patent: Mar. 18, 1986

[54] ENDOSCOPE CONNECTING DEVICE
[75] Inventor: Fumiaki Ishii, Tokyo, Japan
[73] Assignee: Olympus Optical Co., Ltd., Tokyo, Japan
[21] Appl. No.: 724,938
[22] Filed: Apr. 19, 1985

Related U.S. Application Data

[63] Continuation of Ser. No. 470,603, Feb. 28, 1983, abandoned.

[30] Foreign Application Priority Data

Mar. 8, 1982 [JP] Japan ................................. 57-36004

[51] Int. Cl.$^4$ .............................................. A61B 1/00
[52] U.S. Cl. .................................... 128/4; 339/154 A
[58] Field of Search ........................................ 128/4–8;
362/32, 226, 804; 352/198, 200, 203; 354/62,
176, 132; 339/31 R, 31 M, 154 A, 166 R, 170

[56] References Cited

U.S. PATENT DOCUMENTS 4,253,448  3/1981  Terada .................................... 128/4
4,261,345  4/1981  Yamaguchi ............................ 128/6
4,402,313  9/1983  Yabe ...................................... 128/6
4,414,608  11/1983  Furihata .............................. 128/6

Primary Examiner—Edward M. Coven
Assistant Examiner—Max F. Hindenburg

[57] ABSTRACT

A connecting device mechanically and electrically connects a first endoscope having a connector including contact pins projecting at the end surface thereof in an insertion direction and a second endoscope having a connector including contact pins projecting at the outer peripheral surface thereof to a socket of a power source. The connecting device includes an adapter at the endoscope side capable of mechanically connecting to the connector of the second endoscope and an adapter at the power source side provided at the socket of said power source, capable of being selected to mechanically and electrically connect to the connector of the first endoscope and the adapter at the endoscope side. The second endoscope is electrically connected to the socket of the power source through the adapters.

6 Claims, 14 Drawing Figures

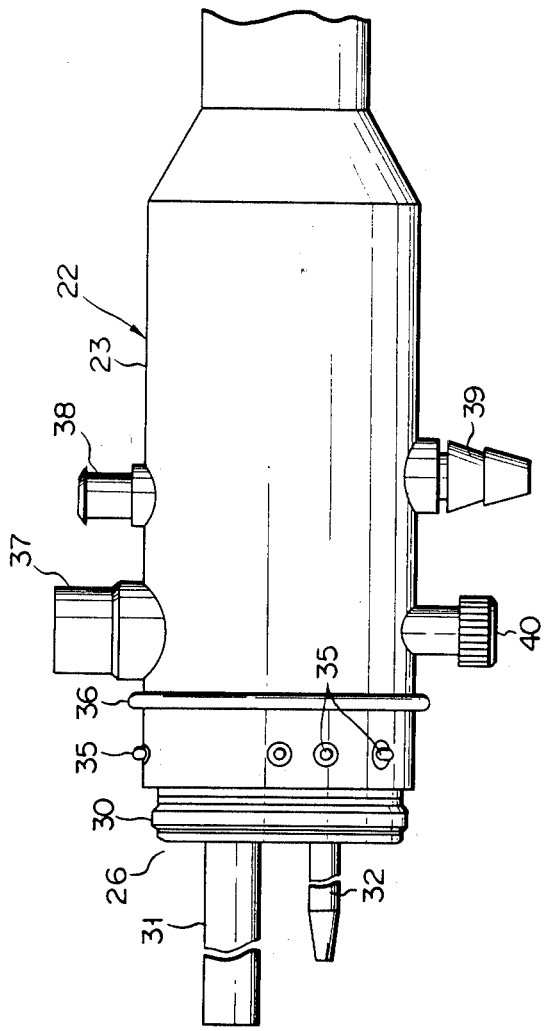

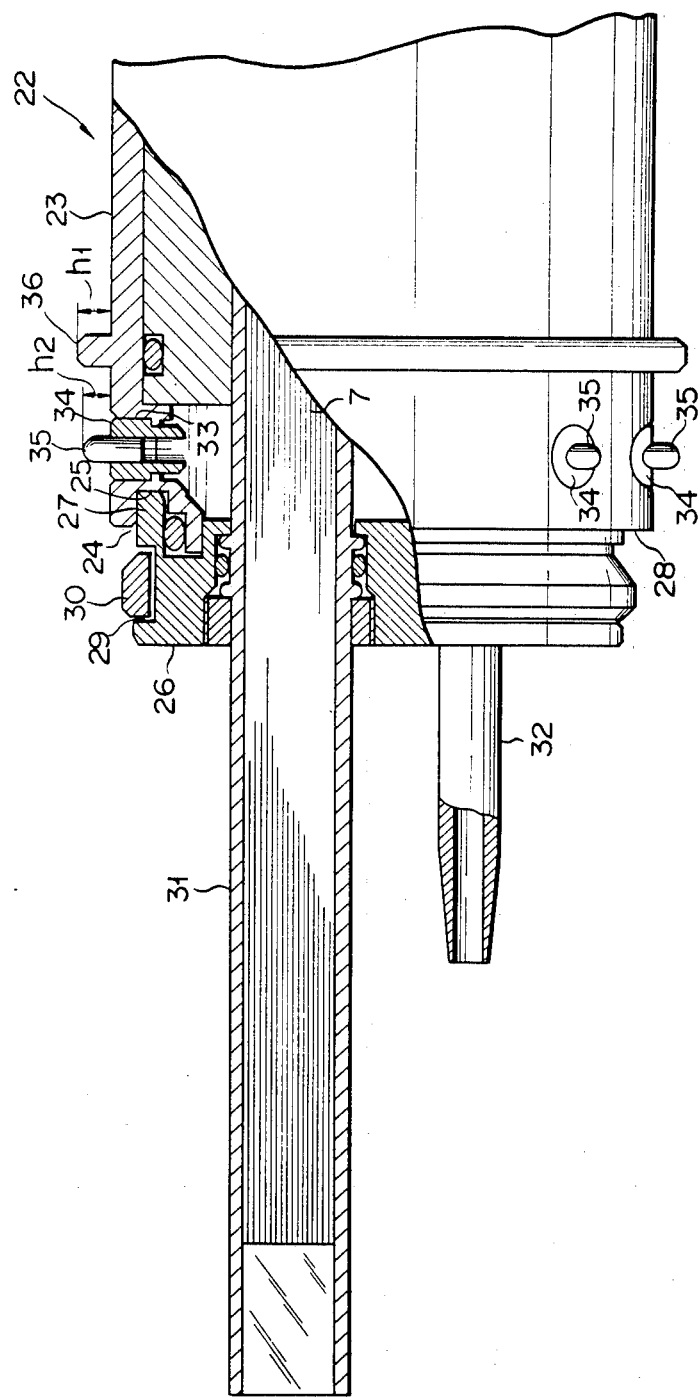

F I G. 4
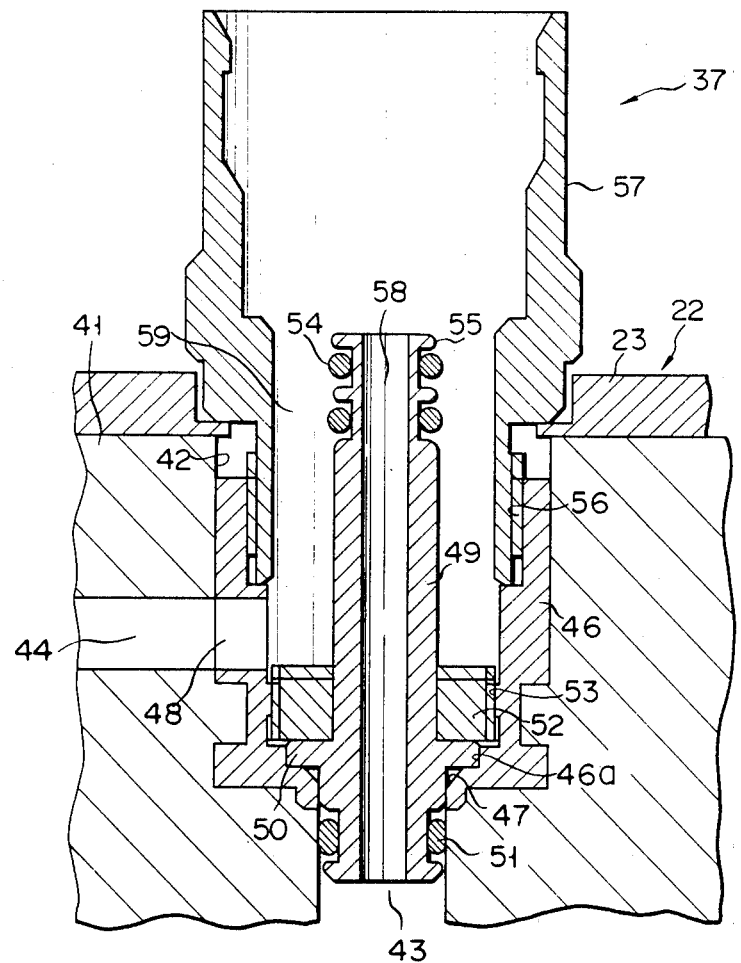

ENDOSCOPE CONNECTING DEVICE

This application is a continuation of application Ser. No. 470,603, filed Feb. 28, 1983, now abandoned.

BACKGROUND OF THE INVENTION

The present invention relates to an endoscope connecting device which connects a connector of an endoscope to a socket of a power source.

A connecting device, which connects a connector provided at a light guide cable of an endoscope to a socket of a power source to electrically and optically conduct the power source to the endoscope and which also enables the connector to be connected to gas and water feeding systems, is known.

The connector has a light guide tube, a gas feeding tube and a plurality of contact pins, which are projected toward a recess portion formed at the end of a connector body. In other words, the base end of the light guide tube, the gas feeding tube and the contact pins are enclosed by an engaging column which is formed with the recess portion.

As endoscope cleaning techniques have recently made progress as well as endoscopes, the entire endoscope has been formed in a waterproof structure and has been dipped in a medical solution for disinfection and irrigation. Since the recess portion is formed at the end of the connection body as described above, and the light guide tube, the gas feeding tube and the contact pins are projected in the recess portion, detergent will remain in the gaps between the tubes and between the pins in the bottom of the recess portion after they are taken out of the detergent, and such detergent cannot be wiped off.

Another connector has been developed in which the entire structure has been altered; the end of the connector body has been formed as a flat surface, a light guide tube and a gas feeding tube have been projected from the flat surface and a plurality of contact pins have been protruded on the outer peripheral surface of the body. Since this connector does not have a recess portion at the body and the light guide tube, and the gas feeding tube and the contact pins project from the outer peripheral surface of the body, detergent adhering to the surface can be readily wiped off after irrigation.

When the structure of the connector is thus entirely altered as described above, the structure of a socket of a power source to be connected to the connector should also be changed to match the connector. However, the power source is expensive, and it is not accordingly economical to prepare a plurality of power sources with different sockets for the altered connectors.

SUMMARY OF THE INVENTION

The present invention has been made in consideration of this and has for its object to provide an endoscope connecting device which is capable of mounting any connector by employing at least two adapters at an endoscope side and a power source side without alternation of the socket of the power source and which is capable of securing interchangeability between the connectors of different type and the power source.

BRIEF DESCRIPTION OF THE DRAWINGS

FIG. 2 is a side view showing the connector of the second endoscope partly eliminated;

FIG. 3 is an enlarged cross sectional view showing the connector partly cut out;

FIG. 4 is an enlarged cross sectional view showing a gas and water feeding base of the connector;

DETAILED DESCRIPTION OF THE PREFERRED EMBODIMENTS

The present invention will now be described in more detail with reference to the accompanying drawings.

Figure 1A:
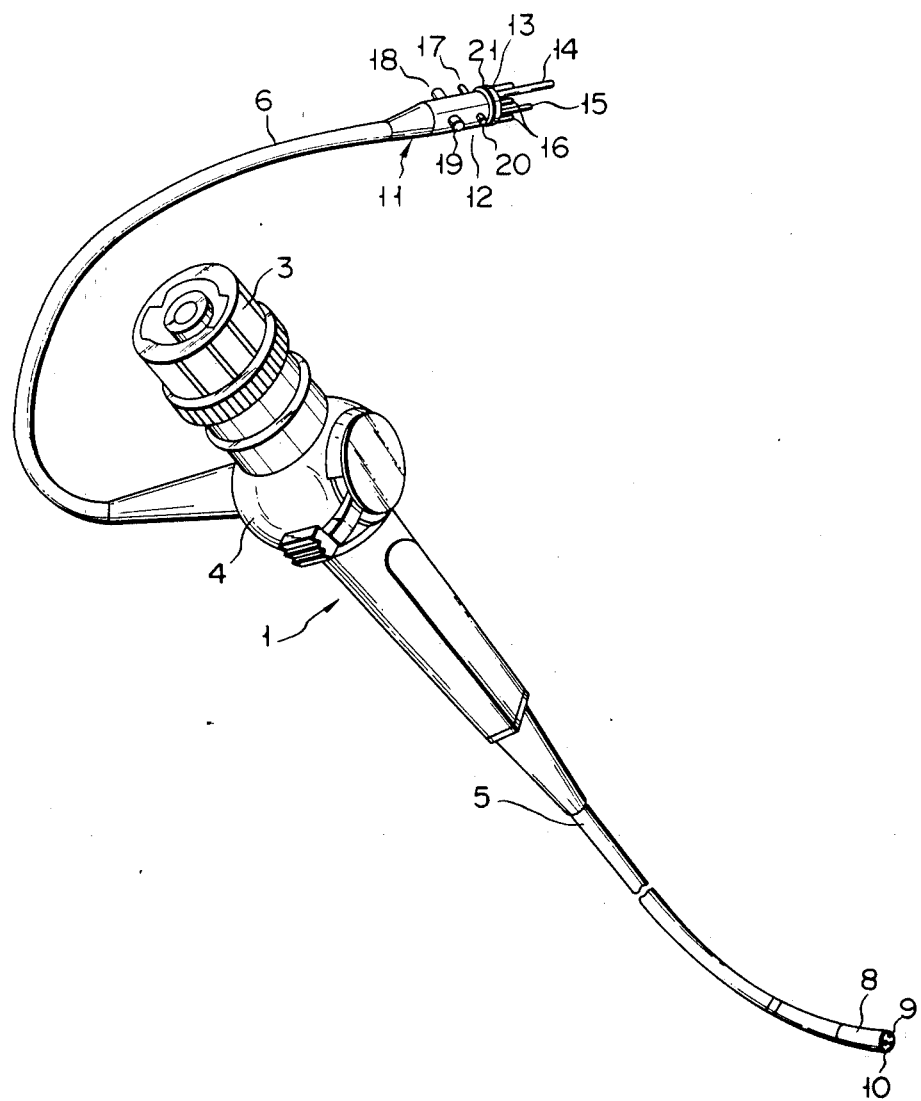
FIGS. 1A and 1B are perspective views showing first and second endoscopes of different types capable of being connected to a power source via a connecting device according to an embodiment of the present invention.
Figure 1B:
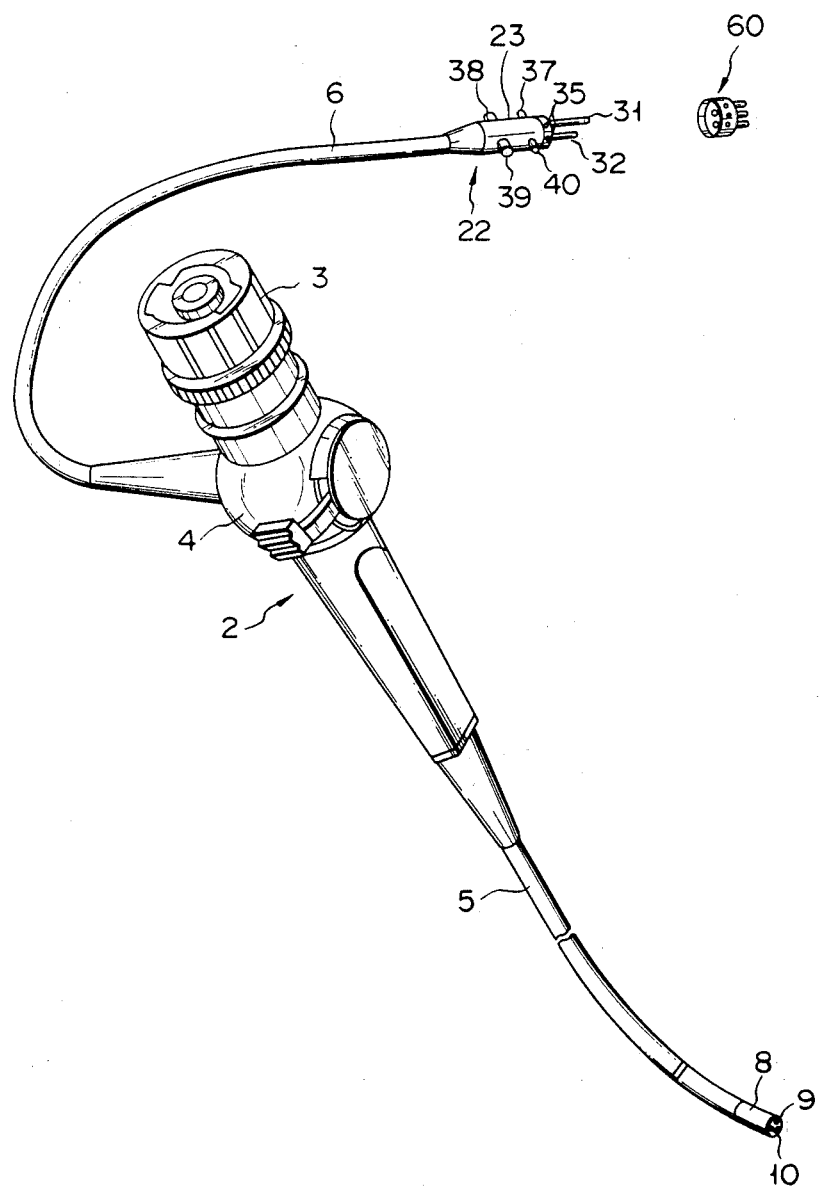

In FIG. 1A, reference numeral 1 designates an endoscope of a conventional type, hereinafter referred to as a "a first endoscope", and in FIG. 1B, reference numeral 2 depicts an endoscope of a novel type, hereinafter referred to as "a second endoscope". These endoscopes 1 and 2 have the same fundamental structure, except for the connectors to be described later. In both the endoscopes 1 and 2, a flexible insert unit 5 and a light guide cable 6 are connected to an operation section 4 which has an eyepiece section 3. A light guide 7 which is formed of an optical fiber bundle, to be described later, is inserted into the cable 6. The light guide is connected to an illumination window 9 of a distal end 8 of the insert section 5 through the operation section 4 and the interior of the insert section 5. An image guide (not shown) which is connected at its one end to the eyepiece section 3 and which is connected at the other end to an observation window 10 of the distal end 8 is inserted into the insert section 5.

A connector 11 is attached to the end of the cable 6 of the endoscope 1. A connector body 12 of the connector 11 is formed in a cylindrical shape. At the end of the body 12 is formed an engaging cylindrical 13 which is formed of a recess portion. This recess portion is opened at the front end face and is closed at the bottom with a bottom wall. At the bottom of the cylinder 13 are projected a light guide tube 14 having the light guide, a gas feeding tube 15 and plurality of contact pins 16 extending outwardly from the opening of th cylinder 13. Further, from the outer peripheral surface of the body 12 are projected a gas and water feeding base 17, a carbon dioxide gas feeding base 18, a suction base 19 and a high frequency earth base 20. An engaging ring 21 is engaged with the outer peripheral surface of the end of the body 12.

A connector 22 which is attached to the end of the cable 6 of the second endoscope 2 is constructed as shown in FIGS. 2 to 4. In FIGS. 2 to 4, reference numeral 23 designates a connector body which is formed in a cylindrical shape. An opening 24 is formed at the end of the body 23. An annular groove 25 is formed at the end face formed with the opening 24 along the edge, and a projecting edge 27 of a circular end plate 26 for blocking the opening 24 is fixedly engaged with the groove 25. This end plate 26 is formed to have a diameter slightly smaller than the body 23, and a stepped portion 28 is formed at the connecting unit. A U-shaped sectional annular groove 29 is formed on the outer peripheral surface of the plate 26, and an engaging ring 30 which is formed of an elastic engaging member such as, for example, an NBR rubber is engaged with the groove 29. At the plate 26 a light guide tube 31 having a light guide 7 therein and a gas feeding tube 32 are projected forwards. Further, a plurality of through holes 33 are opened at a predetermined circumferential interval at the peripheral wall at the end side of the body 23, and a plurality of contact pins 35 are each secured through an insulating bush 34 to the corresponding hole 33. The pins 35 are respectively projected at their ends from the outer peripheral surface of the body 23, and are electrically connected at their base ends to an endoscope camera to transmit and receive a photographing drive signal and a control signal. An annular projection 36 is projected integrally at the outer peripheral surface of the body 23 which is disposed slightly to the rear from the pins 35. The projecting height $h_1$ of the projection 36 is slightly higher than the projecting height $h_2$ of the pin 35. In this manner, even if the connector 22 is laid on a desk or the like, the projection 36 will not contact the desk surface, so the pins 35 are protected.

On the outer peripheral surface of the body 23 are projected a gas and water feeding base 37, a carbon dioxide as feeding base 38, a suction base 39 and a high frequency earth base 40. The base 37 is mounted to the body 23 as follows: a mounting hole 42 is opened radially to the body 23 at the inner body 41 of the body 23. A water feeding hole 43 is opened at the bottom of the hole 42, and a gas feeding hole 44 is opened at the side wall. These holes 43 and 44 communicate with gas and water feeding lines (not shown), respectively. Further, a mounting cylinder 46 is coaxially mounted at the inner peripheral surface of the hole 42. A water feeding hole 47 is opened at the bottom of the cylinder 46 to communicate with the hole 43, and a gas feeding hole 48 is opened at the side wall to communicate with the hole 44. A water feeding tube 49 is inserted into the hole 47. At the tube 49 is formed a collar 50 which is engaged with the step 46a formed at the periphery of the hole 47 of the bottom of the cylinder 46 in the vicinity of the tube 49 and which is hermetically inserted into the inner peripheral surface of the hole 43 through an O-ring 51 which is provided between the base and the inner peripheral surface of the hole 43. Further, a clamping nut 52 which is contacted at its one end with the collar 50 is engaged with the tube 49, and is engaged with threads 53 which are formed on the inner peripheral surface of the cylinder 46. Therefore, the tube 49 is clamped with the nut 52 to the cylinder 46 through the collar 50. The end of the tube 49 extends coaxially with the hole 42 and projects to the opening of the hole 42. At the end of the tube 49 a connecting portion 55 which engages O-rings 54 is integrally formed. Further, threads 56 are formed on the inner peripheral surface at the opening end side of the cylinder 46, and are engaged with the lower small-diameter portion of a connecting cylinder 57 which surrounds the tube 49. A water feeding passage 58 is formed in the tube 49, and a gas feeding passage 59 is formed between the tub 49 and the cylinder 57.

Figure 5:
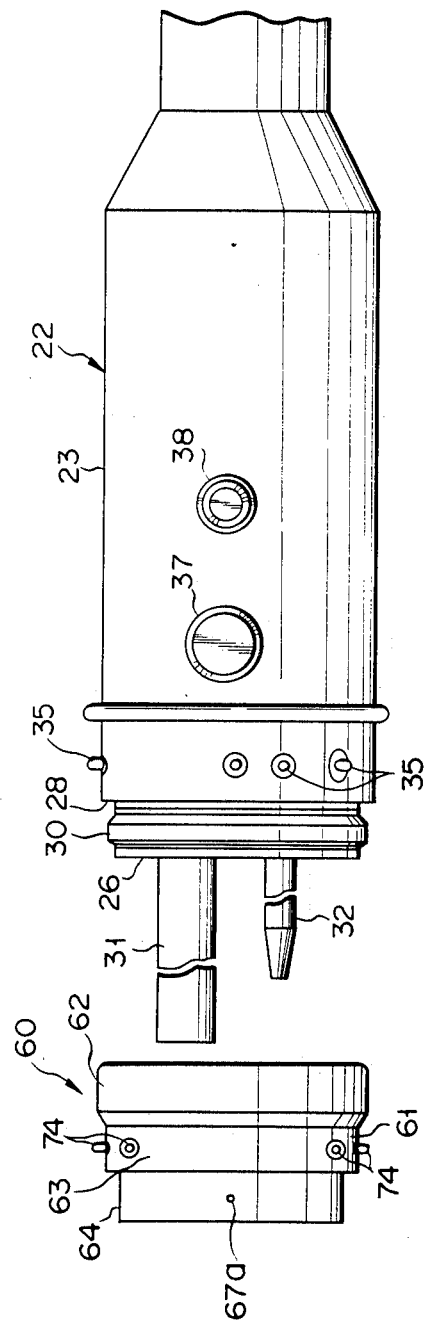
FIG. 5 is a side view showing the exploded connector and an adapter at the endoscope side.
Figure 6:
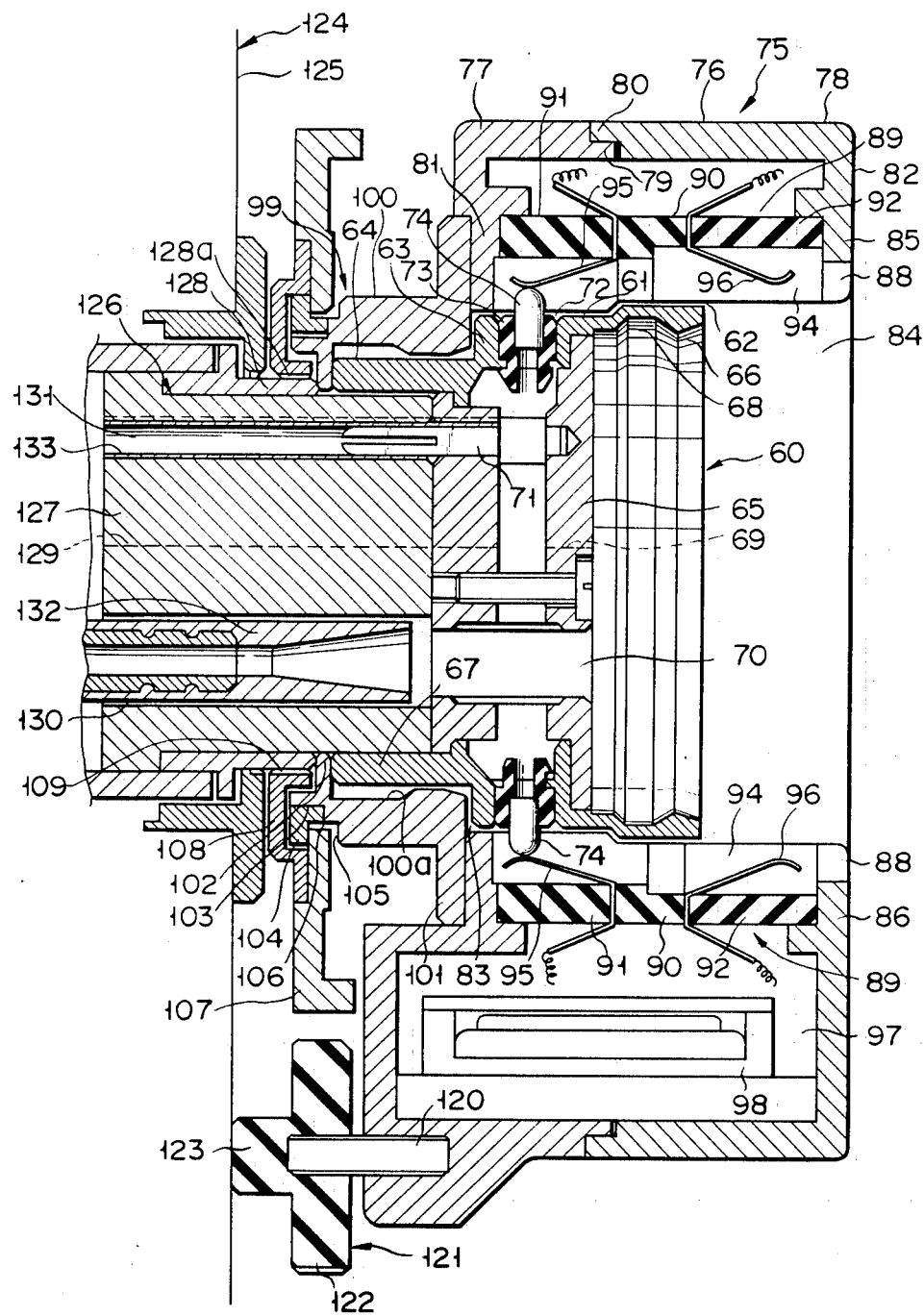
FIG. 6 is a cross sectional view showing a socket, an adapter at the power source side and the adapter at the endoscope side.
Figure 7:
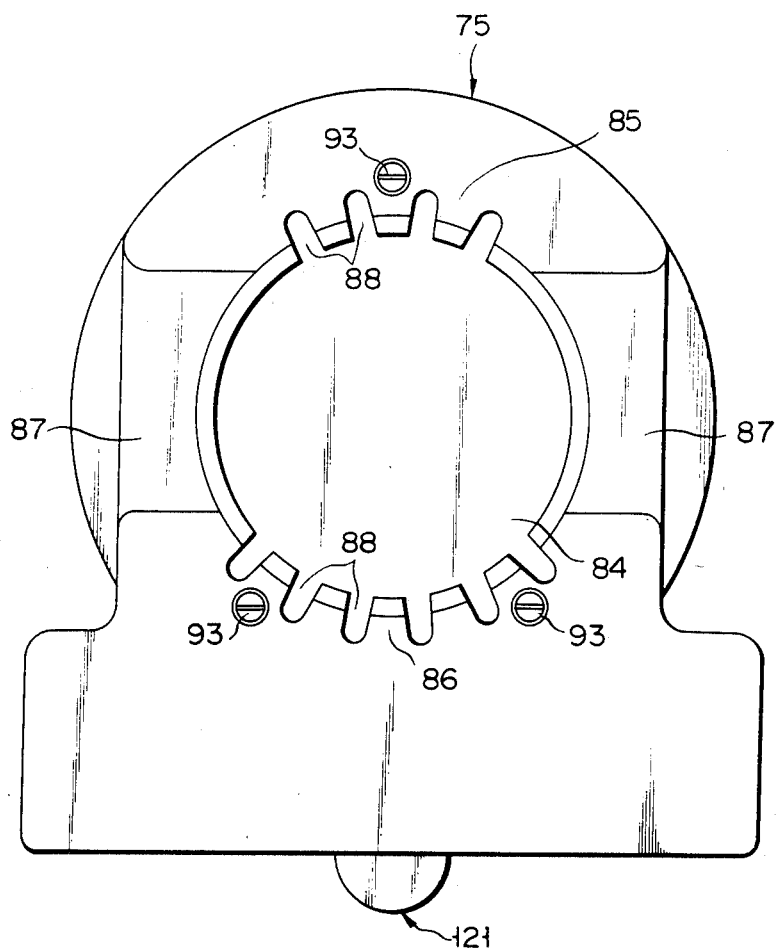
FIG. 7 is a front view of the adapter at the power source side.

An adapter 60 of an endoscope side is detachably mounted at the connector 22 of the endoscope 2 thus constructed. The adapter 60 is constructed as shown in FIGS. 5 and 6. Reference numeral 61 designates a cylindrical unit which is opened at both ends and which is composed of a large-diameter portion 62 disposed at one end side, a small-diameter portion 64 and an intermediate-diameter portion 63. An insulating wall 65 to block the opening is formed at the portion 63, thereby forming an engaging cylindrical portion 66 of the connector side at the large-diameter portion 62 side, and an engaging cylindrical portion 67 of the socket side at the small-diameter portion 64 side. The cylindrical portion 66 is engaged with the plate 26 of the connector 22, and an annular groove 68 which is detachable from the ring 30 is formed on the inner peripheral surface of the cylindrical portion 66. Further, a pair of engaging pins 67a, 67b are projected at an interval of 180° in space on the outer periphery of the cylindrical portion 67 of the socket side. The tubes 31 and 32 pass through holes 69, 70 in the wall 65. When the cylindrical portion 66 is engaged with the connect 22, the front end face of the plate 26 is joined to the wall 65. In addition, a plurality of terminal pins 71 are projected axially at the wall 65 on the cylindrical portion 67 side. A plurality of through holes 72 are opened at a predetermined interval spaced in a circumferential direction from each other on the outer peripheral surface of the intermediate-diameter portion 63 of the cylindrical unit 61. Contact pins 74 are respectively secured to the holes 72 through insulating pins 73, and are respectively electrically connected to the pins 71.

The adapter 60 is detachably connected to an adapter 75 of the power source side, shown in FIGS. 6 to 10. A body 76 of the adapter 75 is composed of front and rear cases 77 and 78 divided longitudinally. The cases 77 and 78 are engaged with each other with engaging steps 79 and 80, and openings 83 and 84 are respectively formed at the front wall 81 of the case 77 and at the rear wall 82 of the case 78. Further, a small circular portion 85 is formed at the upper edge which forms the opening 84 of the case 78, a large circular portion 86 is formed integrally with the lower edge which forms the opening 84 of the case 78, and notched openings 87 are formed at both sides between the portions 85 and 86. A plurality of notched grooves 88, to which the pins 35 and 74 of the connector 22 and the adapter 60 are respectively inserted, are formed at the positions corresponding to the intervals of the pins 35 and 74 at the inner edges of the circular portions 85 and 86. Further, an insulating terminal base 89 which is formed in a circular-arc shape along the curvature of the circular portions 85 and 86 is formed at the circular portions 85 and 86 between the cases 77 and 78. The base 89 is divided into three sections of an intermediate member 90 and two end members 91 and 92 formed at both ends of the member 90, and these members are interposed between the front wall 81 of the case 77 and the rear wall 82 of the case 78 to be contacted at both ends with the members. The members 90, 91 and 92 are clamped with a clamping bolt 93 which passes through the members together with the cases 77 and 78. Moreover, a plurality of guide grooves 94 which correspond to the grooves 88 are longitudinally formed on the inner peripheral surfaces of the members 90, 91 and 92. Terminal boards 95 and 96 which are simultaneously interposed when assembling the members between the cases 77 and 78, are mounted between the members 90 and 91, and between the members 90 and 91, and between the members 90 and 92. The boards 95 and 96 are formed of leaf springs, one end of each board 95 and 96 is bent in circular-arc shape and is contained in the grooves 94, and the other ends are projected outside the base 89. Further, a space 97 which is surrounded by the cases 77 and 78 is formed outside the base 89 formed at the circular portion 86, and an electric circuit 98 to be described later is secured to the space 97.

A connecting cylinder 99 which is projected forwards is provided at the wall 81 in the case 77 of the adapter 75 of the power source side thus constructed. The cylinder 99 is formed of a cylindrical portion 100 and a mounting collar 101, and the collar 101 is secured to the case 77 with the bolt 93 for clamping the cases 77 and 78. The cylindrical portion 100 is formed in the bore which is engaged with the cylindrical portion 67 of the adapter 60. A stop 102 which defines the inserting length of the end of the cylindrical portion 67 is formed integrally with the inside of the end of the cylindrical portion 100 in contact with the end of the cylindrical portion 67. Moreover, threads 103 are formed on the outer peripheral surface of the end of the cylindrical portion 100, and are engaged with a mounting annular unit 104. An annular recess 106 is formed between the unit 104 and a step 105 formed on the outer periphery of the cylindrical portion 100. The inner periphery of a clamping ring 107 is inserted into the recess 106 to be supported rotatably. Further, a clamping ring 108 is mounted coaxially and integrally with the front part of the ring 107. The ring 108 has a recess, to which the end of the cylindrical portion 100 and the unit 104 are inserted, and which is formed at the front part of the cylinder 99. Female threads 109 are formed on the inner peripheral surface of the recess.

Figure 8:
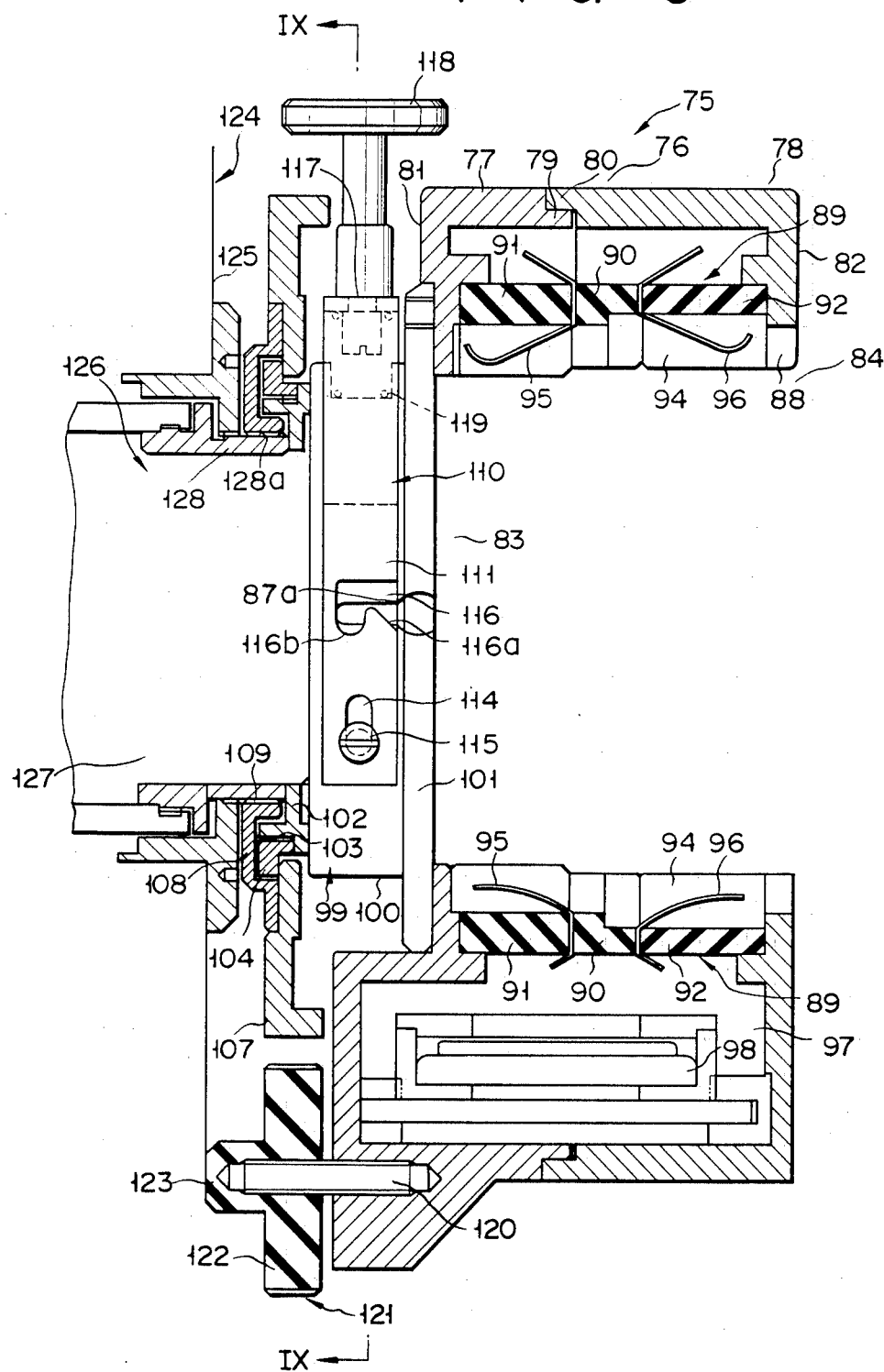
FIG. 8 is a side view partly eliminated of the adapter at the power source side partly cut out.
Figure 9:
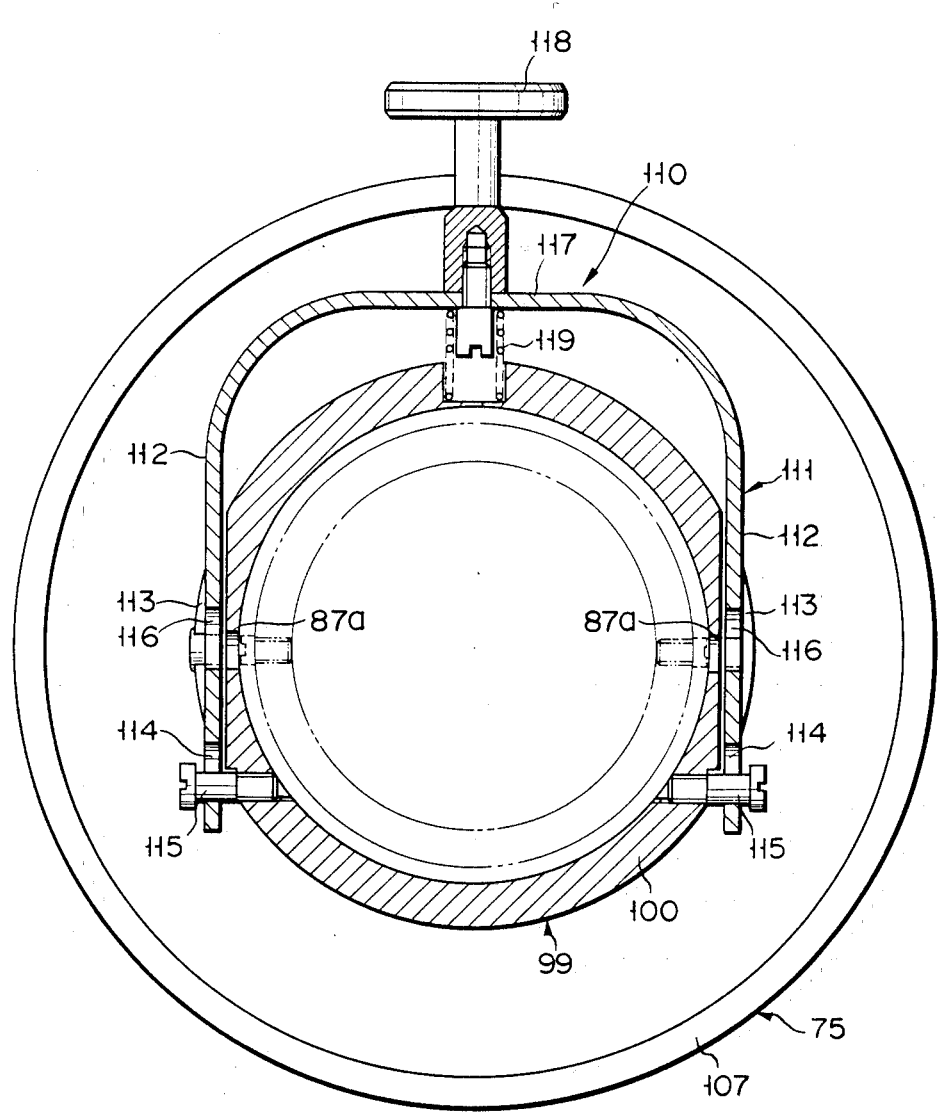
FIG. 9 is a cross sectional view along the line IX—IX in FIG. 8.
Figure 10:
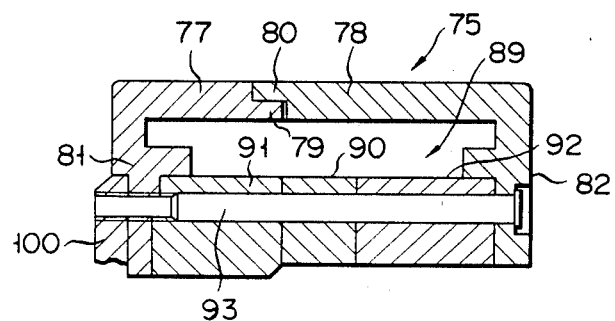
FIG. 10 is a cross sectional view showing the associated state of an insulating terminal base.

A locking mechanism 110 shown in FIGS. 8 and 9 is provided outside the cylinder 99. This mechanism 100 has, as shown in FIG. 9, a movable member 111 which is formed by bending a metal plate member in an inverted U shape, and both legs 112 of the member 111 are vertically and slidably inserted into slide grooves 113 which are formed on both side walls of the cylinder 99. Long holes 114 which extend vertically are opened at the lower ends of both the legs 112, and guide pins 115 which are projected from the cylinder 99 are respectively movably inserted into the holes 114. Engaging holes 116 are formed at the intermediate portions of both the legs 112 and hence at the portions corresponding to a pair of engaging slots 87a formed in the adapter 75. The holes 116 are formed substantially in an L shape. An oblique surface 116a is formed on the lower surface in the vicinity of the openings 87 at the position of the rear end side, and a recessed part 116b is formed in the depth, to be capable of being connected with the pin 67a of the adapter 60. Further, an unlocking lever 118 which is projected upward is mounted at the head 117 of the member 111. A compression spring 119 is interposed between the head 117 and the recess formed at the top of the cylinder 99 to always urge the member 111 upward, i.e., in a direction so that the pin 67a engages with the recessed part of the engaging hole 116.

A threaded shaft 120 which is projected forward is projected at the lower front surface of the case 77 of the adapter 75. A pressing member 121 which is formed of a synthetic resin material or rubber is rotatably engaged with the shaft 120. The member 121 is composed of a large-diameter operating portion 122 which is knurled on the outer peripheral surface. A small-diameter contacting portion 123 which is formed integrally with the front surface of the operating portion 122, moves telescopically upon rotating with respect to the shaft 120, and holds the adapter 75 with the contacting portion 123 in contact with a power source, to be described later.

In FIG. 6, reference numeral 124 designates a power source, in which a photographing drive power source circuit, an exposure control circuit and an illumination lamp (all not shown) are contained. A socket 126 is provided at the front panel 125 of the power source 124. A body 127 of the socket 126 is mounted with a mounting ring 128 having male threads 128a partly projecting forward from the panel 125. Further, there is a light guide tube inserting hole 129, a gas feeding tube inserting hole 130 and a plurality of contact pin inserting holes 131 in the body 27. An illumination lamp faces the hole 129, a gas feeding pipe 132 is inserted into the hole 130, and electric connection terminal 133 is inserted into the holes 131.

Figure 11:
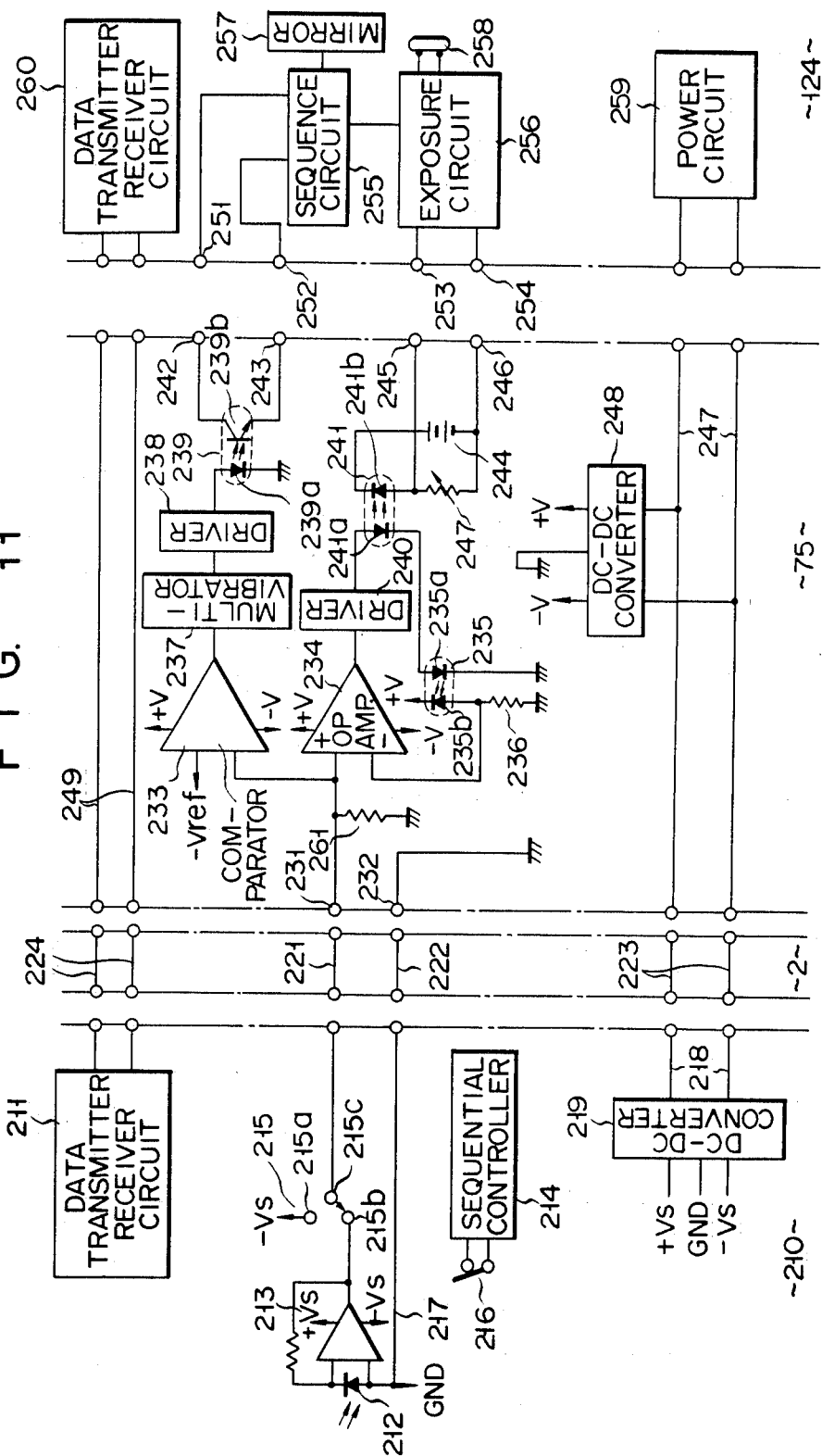
FIG. 11 is an electric circuit diagram of the connecting device, the power source and a camera for the endoscope.

The electric circuit system of the endoscope will be described referring to FIG. 11. In FIG. 11, a photodetector 212 which receives part of the reflected light incident to the camera 210 of an object to be photographed and which outputs a photoelectric signal corresponding to the reflected light of the object, is provided. The photodetector 212 is connected to an amplifier 213. A first stationary contact 215a of a changeover switch 215 which is driven by a sequential controller 214 is connected to a power source voltage −Vs, and a second stationary contact 215b is connected to the output terminal of the amplifier 213. A synchro switch 216 of the camera 210 is connected to the controller 214. The controller 214 drives the switch 215 in response to the operating state of the switch 216. A movable contact 215c of the switch 215 and a ground line 217 are respectively connected to a terminal 231 of the adapter 75 and a ground terminal 232 through the signal transmission lines 221 and 222 of the endoscope 2. The terminal 231 is connected to one input terminal of a comparator 233 and a non-inverting input terminal of an operational amplifier 234. A reference power source votage −Vref is connected to the other input terminal of the comparator 233. An inverting input terminal of the amplifier 234 is connected to a power source voltage +V through a photodiode 235a of a photocoupler 235, and is grounded through a resistor 236. The output terminal of the comparator 233 is connected to an LED driver 238 through a one-shot multivibrator 237. The output terminal of the driver 238 is grounded through an LED 239a of a photocoupler 239. The output terminal of the amplifier 234 is connected to an LED driver 240, and the output terminal of the driver 240 is grounded through an LED 241a of a photocoupler 241 and the LED 235a. The collector and the emitter of a phototransistor 239b of the photocoupler 239 are respectively connected to terminals 242 and 243. The cathode of the photodiode 241b of the photocoupler 241 is connected to the positive electrode of a bias power source 244. The anode of the photodiode 241b is grounded to a terminal 245 and is respectively connected to the negative electrode of the power source 244 and a terminal 246 through a variable resistor 247.

The terminals 242, 243, 245 and 246 are respectively connected to terminals 151, 152, 153 and 154 of the power source 124. The terminals 251 and 252 are connected to a photographing sequence circuit 255, and the terminals 253 and 254 are connected to an automatic exposure circuit 256. The sequence circuit 255 is constructed to perform the operating sequence control of an optical path switching mirror 257 and the automatic exposure circuit 256, and the exposure circuit 256 is constructed to emit or stop the emission of a strobe tube 258 in response to the automatic exposure value. The power source line 247 of the power source 124 is connected to a power source line 247 of the adapter 75 and to a power source line 218 of the camera 210 through the power source line 223 of the endoscope 2. A DC/DC converter 219 is connected to the line 218 of the camera 210. A DC/DC converter 248 is connected to the line 247 of the adapter 75.

A data transmitter/receiver circuit 11 of the camera 210 is connected to a data transmitter/receiver circuit 260 of the power source 124 through a transmission line of the endoscope 2 and a transmission line 249 of the adapter 75. The circuits 211 and 260 are constructed to transmit and receive data between the camera 210 and the power source 124. For example, data such as sequential program data and photographing data are transmitted and received. Reference numeral 261 designates an input resistor. When the camera 210 is removed from the endoscope 2, or when the endoscope 2 is removed from the adapter 75, the resistor 261 prevents the entrance of a noise to the terminal 231.

Figure 12:
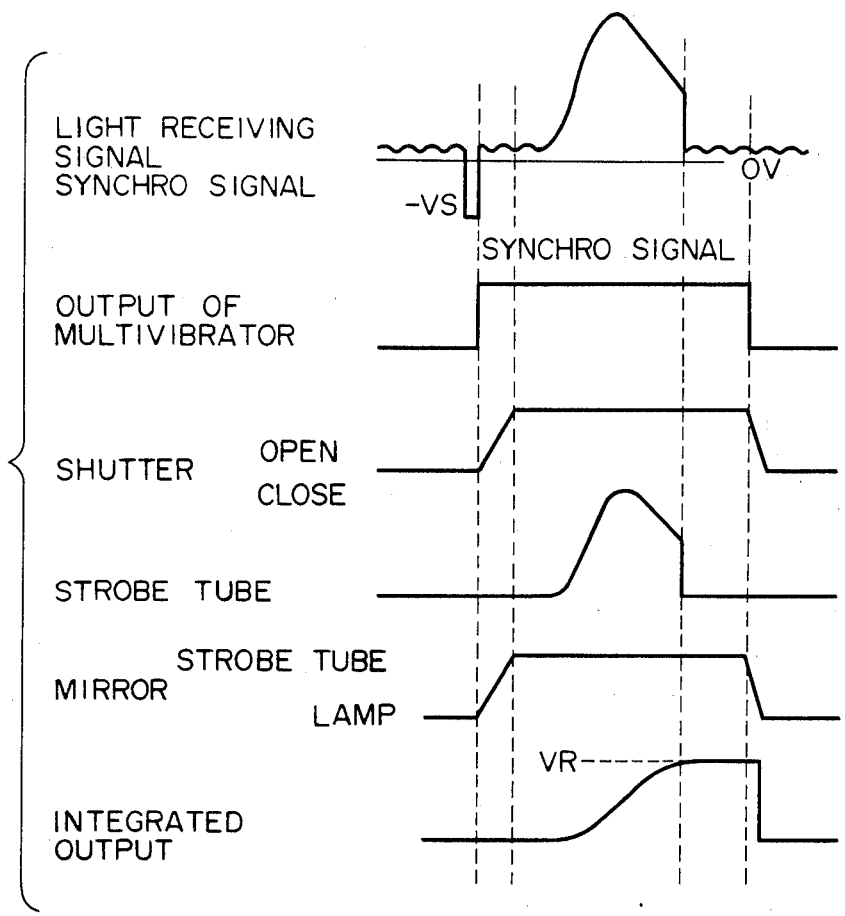
FIG. 12 is a timechart for describing the operation of the electric circuit in FIG. 11.

The operation of the electric circuit thus arranged will be described with reference to the timechart in FIG. 12. When the camera 210 is not released, the controller 214 connects the second contact 215b of the switch 215 to the contact 215c. At this time, the photodetector 212 generates a photoelectric signal (photodetecting signal) corresponding to a diagnostic illumination light. The signal is transmitted through the amplifier 213 and the contact 215b to the line 221 of the endoscope 2. When the camera 210 is released, the switch 216 is closed, and the controller 214 instantaneously switches the contact 215c of the switch 215 to the contact 215a side. In this manner, a voltage signal of −Vs is transmitted as a synchro signal to the line 221 of the endoscope 2. When this synchro signal is applied through the line 221 to the comparator of the adapter 75, the comparator 233 generates an output signal, which in turns triggers the multivibrator 237. The multivibrator 237 thus produces a pulse signal having a predetermined pulse width. The driver 238 allows the LED 239a of the photocoupler 239 to emit a light in response to the pulse signal of the multivibrator 237. At this time, a shutter, and hence a camera shutter (not shown), of the camera 210 starts opening. The phototransistor 239b produces an output signal upon emission of the light from the LED 239a, and the output is supplied as a synchro signal to the photographing sequence circuit 255. The circuit 255 switches the mirror 257 to the optical path of the tube 258 in response to the synchro signal. When the camera shutter is completely opened and the mirror 257 is completely switched to the optical path, the circuit 255 sets an integrating circuit (not shown) of the circuit 256 and operates a light emitting circuit (not shown) of the tube 258. When the tube 258 emits a light, the photoelectric signal of the photodector 211 of the camera 210 increases in response to the emission of a strobe. This photoelectric signal is supplied through the contact 215b of the switch 215 and the line 221 of the endoscope 2 to the amplifier 234. The amplifier 234 supplies an output signal responsive to the photoelectric signal to the driver 240. The driver 240 allows the LEDs 241a and 235a of the photocouplers 241 and 235 to emit lights in response to the output signal of the amplifier 234. The photocoupler 235 substantially feeds back the output of the amplifier 234 by photocoupling, and the photocoupler 241 transmits the output of the amplifier 234 to the terminals 245 and 246. The output signal of the amplifier 234 transmitted through the photocoupler 241 is supplied as a photodetection signal through the terminals 245, 246 and 253, 254 to the circuit 256. The integrating circuit of the circuit 256 integrates the signal. When the integrated output of the integrating circuit reaches the reference value $V_R$, the tube 258 is deenergized to stop emitting the light. Thereafter, when the pulse signal of the multivibrator 237 falls, the camera shutter is closed, and the mirror 257 is switched to the diagnostic illumination light path. In this manner, an automatic exposure photographing of one frame has been performed.

According to the endoscope thus constructed and operated as described above, the photocouplers 235, 239 and 241 are provided at the adapter 75, and the synchro signal and the photoelectric signal (photodetection signal) are transmitted by optical coupling. Therefore, the synchro signal and the photoelectric signal can be transmitted accurately without adverse influence of electric noise.

The operation of the endoscope connecting device constructed as described above will now be described. In the case that the adapter 75 is mounted to the socket 126 of the power source 124, the ring 108 of the adapter 75 is first engaged with the ring 128 of the socket body 127. In this state, the ring 107 is turned in a predetermined direction, to rotate integrally with the ring 108, and the threads 128a of the ring 128 are engaged with the threads 109 of the ring 108. Accordingly, the cylinder 99 is engaged at the interval with the outside of the body 127 through the ring 104 to be engaged with the ring 107, and the adapter 75 is secured to the socket 126. When the operating portion 122 of the member 121 is rotated by fingers, or the like, in this state, the member 121 moves forward since the member 121 is engaged with the shaft 120, and the contacting portion 123 makes contact with the front panel 125 of the power source 125. When the member 121 is further rotated, the contacting portion 123 is pressurized on the front panel 125, resulting in an increase in the frictional resistance between the contacting portion and the panel, thereby improving the coupling strength of the connecting portion between the socket 126 and the adapter 75.

When the endoscope 1 is first used with the adapter 75 mounted to the socket 126 of the power source 124, the connector 11 is inserted into the opening 84 of the adapter body 76. At this time, the bases 17, 18, 19 and 20 project from the connector 12. Since the openings 87 are, however, formed at the inner peripheral surface of the body 76 as an escaping portions, these bases do not interfere with the body 76. Therefore, the connector 11 passes through the body 76. The tubes 14 and 15 and the pins 16 are respectively inserted into the holes 129, 130 and 131. Then, the tube 15 is connected to the pipe 132, and the pins 16 are electrically connected to the terminal 133. In other words, the ring 21 is engaged with the groove 100a formed on the inner peripheral surface of the cylindrical portion 100 to be mechanically held, and the endoscope 1 is electrically and optically connected to the power source 124.

Then, when the endoscope 2 is used the adapter 60 is first mounted to the connector 22. In other words, the tubes 31 and 32 which are projected from the plate 26 of the connector 22 are respectively inserted into the holes 69 and 70 of the adapter 69, and the plate 26 is further press-fitted into the cylindrical portion 66. When the plate 26 is press-fitted until the end face of the cylindrical portion 66 makes contact with the step 28 of the connector body 23, the ring 30 is elastically engaged with the groove 68, and the connector 22 is coupled integrally with the adapter 60.

When the connector 22 is inserted together with the adapter 60 into the adapter 75 mounted at the socket 126 in this state, the tube 31 projected through the adapter 60 is inserted into the hole 129 of the socket 126, and the tube 32 is inserted into the hole 130. Further, the pins 74 and 35 of the adapter 60 and the connector are respectively inserted into the grooves 94 through the grooves 88. Therefore, the pins 74 and 35 are respectively connected to the terminal boards 95 and 96 to be electrically connected. Simultaneously, the cylindrical portion 67 of the adapter 60 is engaged with the body 127, allowing the wall 65 to be joined with the front end face of the body 127. The tubes 31 and 32 and the pins 71 are respectively inserted into the holes 129, 130 and 131. The tube 32 is connected to the pipe 132, and the pins 71 are electrically connected to the terminal 133. Accordingly, the endoscope 2 is electrically and optically connected to the power source 124. When the connector 22 is inserted into the socket 126 together with the adapter 60, the pin 67a projected to the adapter 60 passes through the engaging slots 87a and then faces the hole 116 of the mechanism 110. When the pin 67a contacts the surface 116a upon insertion of the connector 22 and is further press-fitted, the pin 67a slides on the surface 116a. Thus, the member 111 is pressed down against the recoiling strength of the spring 119, and when the pin 67a falls in the recessed part 116b, it is raised by the urging strength of the spring 119, and the pin 67a is engaged with the hole 116. Accordingly, the adapter 60 is locked to the adapter 75 through the pin 67a so as not to be detachable. Further, when the connector 22 is removed from the socket 126 of the power source 124 after the endoscope 2 is used, the connector 22 is isolated from the adapter 60 by pulling the connector 22, and is then pulled from the socket 126. Since the adapter 60 is locked to the adapter 75 by the mechanism 110 at this time, the adapter 60 is not removed but is maintained in the adapter 75. Therefore, when the endoscope 2 is used again, the connector 22 can be electrically and optically connected similarly to the above operation by inserting the adapter 60 into the adapter 75. Further, when the adapter 60 is removed from the adapter 75 together with the connector 22, the pins 67a and the recessed part 116b are disengaged by pressing the member 111 against the urging strength of the spring 119. Thus, the adapter 60 can be removed integrally with the connector 22 by pulling the connector 22 when the lever 118 is depressed.

As described above, the connector 11 of the endoscope 1 can be connected by mounting the adapter 75 to the socket 126 of the power source 124. The endoscope 2 can be connected by inserting the adapter 75 to the connector 22 through the adapter 60 when using the endoscope 2, thereby maintaining the interchangeability between the endoscopes 1 and 2. Further, the connector 22 of the endoscope 2 has a flat end surface, the tubes 31 and 32 project from the flat surface, and the pins 35 project from the outer peripheral surface in the waterproof structure. Therefore, the endoscope can be dipped into detergent to clean it, and since there are no recess portions like the connector 11 of the endoscope 1, no detergent accumulates in the connector after removal, and the connector can be readily wiped clean.

Figure 13:
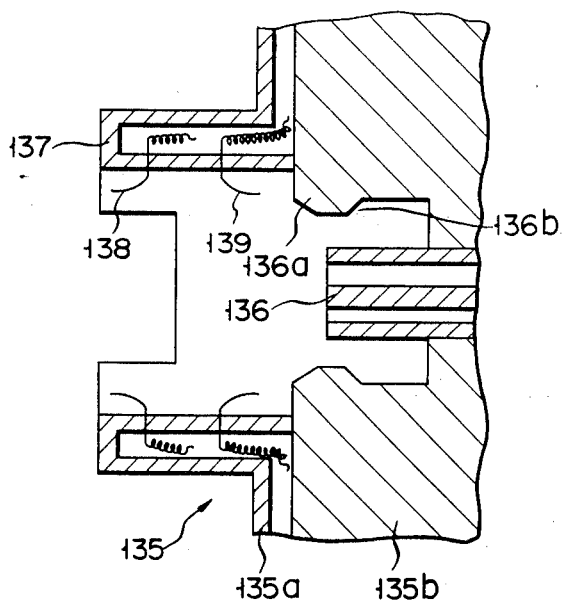
FIG. 13 is a sectional view showing another embodiment of the present invention.

In the embodiment described above, the adapter 75 is constructed to be detachable from the socket 126 of the power source 124. However, as shown in FIG. 13, the adapter 134 may be constructed integrally with the socket 136 of the power source 135. A circular groove 136b, with which the engaging ring 21 of the connector of the first endoscope is engaged, is formed on the inner surface of a metal base 136a, in which the socket 136 of the power source 135 is inserted. A cylindrical adapter body 137 made of an insulating material may be projected integrally from the front panel 135a of the power source 135. Terminals 138 and 139 are aligned on the inner peripheral surface of the adapter body 137 and contact pins 35 of the endoscope 2 and contact pins 74 of the adapter 60 are electrically connected.

According to the present invention as described above, the adapter at the power source side is integral with or detachably mounted to the socket of the power source, and the adapter at the endoscope side is detachably provided on the adapter at the power source side. Therefore, the connector which has the contact pins projecting from the end face in the inserting direction and the connector which has the contact pins projecting from the outer peripheral source may be selectively connected to the above socket, and the interchangeability can be maintained without altering the structure of the socket to the connector.

What is claimed is:

1. A connecting device for selectively connecting a first endoscope and a second endoscope to the same socket of a power source mechanically and electrically, said first endoscope having a connector including contact pins projecting at an end recessed surface thereof in a direction in which the pins can be inserted into the socket and said second endoscope having a connector with a flat end surface and including contact pins projecting at an outer peripheral surface thereof comprising:

a first adapter constructed such that it is capable of mechanically being connected to the connector of said second endoscope; and a second adapter constructed such that it is capable of being connected to the socket of said power source, said second adapter being also constructed such that it it capable of being selectively connected to said connector of said first endoscope and said connector of said second endoscope with said first adapter thereon mechanically and electrically, said second adapter being formed in a cylindrical shape and comprising a body capable of receiving therein said first adapter and the connector of said second endoscope; and said second adapter comprises first terminal boards elastically projecting from inner peripheral surfaces thereof and located to be electrically connected to the contact pins of said second endoscope when said second adapter is connected to said second endoscope and second terminal boards elastically projecting from inner peripheral surfaces of said second adapter electrically connected to said first terminal boards; and said first adapter comprises a cylinder having an outer diameter substantially smaller than the inner diameter of said second adapter, first terminal pins projected from the outer peripheral surface of the cylinder to be electrically connected to said second terminal boards of said second adapter when said second adapter is connected to said first adapter and second terminal pins projected from one end surface of the cylinder electrically connected to said first terminal pins of said first adapter to be electrically connected to the socket when said second adapter is connected to said socket and first adapter; and the body of said second adapter comprises a plurality of guide grooves formed on the inner peripheral surface thereof and extending along an axial direction, the first terminal pins of said first adapter being slidable along the guide grooves in the grooves upon insertion of the first adapter into the second adapter, and the second terminal boards of said second adapter projecting into the guide grooves.

2. The connecting device acccording to claim 1, wherein the body of said second adapter comprises a rear case, a front case connected to said rear case, and an insulating terminal base of cylindrical shape connected to said cases and provided at a predetermined interval from the inner peripheral surfaces of said cases, and said terminal boards being respectively secured to the terminal base so that both ends are inwardly and outwardly projected.

3. The connecting device according to claim 1, wherein said device further comprises locking means for locking the mechanical connection of said second adapter and said first adapter.

4. The connecting device according to claim 3, wherein said locking means comprises an engaging pin projected to said first adapter, a member having an engaging hole engaged with said engaging pin when said second adapter is connected to said first adapter, and an operating member capable of releasing the engagement of said engaging pin with said engaging hole by moving said member.

5. The connecting device according to claim 1, wherein said device further comprises a pressing member projected from said second adapter for holding said second adapter in contact with said power source, said pressing member moving telescopically by rotating same with respect to said second adapter.

6. A connecting device for respectively connecting a first endoscope and a second endoscope to the same socket of a power source mechanically and electrically, said first endoscope having a connector including contact pins projecting at an end recessed surface thereof in a direction in which the pins can be inserted into the socket, and said second endoscope having a connector with a flat end surface and including contact pins projecting at an outer peripheral surface thereof comprising: a first adapter capable of mechanically being connected to the connector of said second endoscope, a second adapter provided at the socket of said power source capable of being selectively connected to said connector of said first endoscope and said first adapter mechanically and electrically, said second adapter being formed in a cylindrical shape and comprising a body capable of receiving therein said first adapter and the connector of said second endoscope, said first adapter comprising a cylinder having an outer diameter substantially smaller than the inner diameter of said second adapter, first and second terminal boards elastically projecting from inner peripheral surfaces of said second adapter, said first terminal board being electrically connected to a contact pin of said second endoscope and said second terminal board being electrically connected to said first terminal board, a first terminal pin projected from the outer peripheral surface of the cylinder of the first adapter and electrically connected to said second terminal board, a second terminal pin projected from one end surface of the cylinder of the first adapter and electrically connected to said first terminal pin and capable of being electrically connected to the socket, and said body of said second adapter comprising a plurality of guide grooves formed on the inner peripheral surface thereof and extending along an axial direction, the first terminal pin of said first adapter being slidable along a guide groove in the groove upon insertion of the first adapter into the second adapter, and the second terminal board of said second adapter projecting into the guide groove.

* * * * *